Oct. 20, 1970 R. S. MOORE Plant Pat. 2,991
MINIATURE ROSE PLANT
Filed Sept. 30, 1968
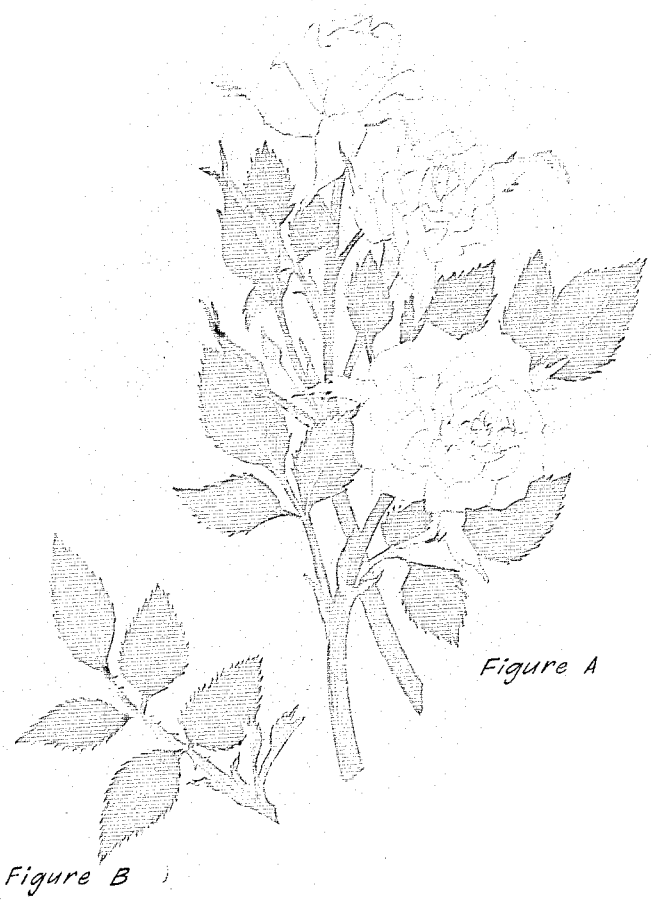
WITNESS
Jeanette Nunn Copley
INVENTOR
Ralph S. Moore United States Patent Office Plant Pat. 2,991
Patented Oct. 20, 1970

2,991
MINIATURE ROSE PLANT

Ralph S. Moore, 2519 E. Noble Ave.,
Visalia, Calif. 93277

Filed Sept. 30, 1968, Ser. No. 763,992
Int. Cl. A01h 5/00
U.S. Cl. Plt.—7 1 Claim The present invention relates to a new and distinct variety of hardy, dwarf, bush type rose plant of the miniature class; the variety being primarily characterized—as to novelty—by clear lavender or pinkish lavender buds and flowers which in general color effect are soft to medium lavender.

The variety is further characterized by:

An abundance of bloom, with flowers borne singly or several to the stem in loose clusters.

Moderate sweet fragrance.

A plant which is vigorous, of rounded spreading shape and with semi-glossy, moderately small foliage with pointed leaflets; the flowers and foliage being similar in size to the variety Easter Morning (U.S. Plant Pat. No. 2,177). The plant, which has a normal height of 10 to 12 inches can easily be maintained at 8″ or less by occasional trimming.

A plant which grows and blooms satisfactorily both in greenhouses and outdoors; is good for growing in pots; and provides excellent garden decoration as well as cut flowers.

The present variety of miniature rose was originated by me at my nursery located at Visalia, Calif., under conditions of careful control and observation, as a cross between Ellen Poulsen (a polyantha rose, not patented) as the seed parent and Debbie (miniature, patent applied for) as the pollen parent.

Subsequent to origination of the variety I successfully asexually reproduced it, in my nursery located as aforesaid, by budding as well as by cuttings; the reproductions having run true in all respects.

The figure of the drawing illustrates a spray, including foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bush; seeding; greenhouse; outdoors; cut flowers; garden decoration; potted plant.

Class: Miniature.

Flowers:

*Continuity.*—Continuous; repeat bloom all season.

*Fragrance.*—Moderate.

Flowers borne: Singly and several together (3 to 5) on strong medium length stems.

Quantity of bloom: Abundant both outside and in greenhouse.

Bud: Peduncle—medium length; slender but sturdy; erect; medium green, sometimes tinted bronze; few to numerous very small soft hairs. Before calyx breaks: size—small. Form medium long; pointed; with foliaceous appendages and numerous tiny short hairs on surface of bud; with foliaceous parts extending beyond the tip of the bud equal to one half or more of its length. Color—medium green, occasionally tinted with bronze. As calyx breaks: color—lavender or pinkish lavender. As first petal opens: same color but showing yellow or brownish tones near base of petal; size small.

Bloom:

*Size.*—When fully open—small, averaging 1¼″ to 1½″.

*Petalage.*—Double—40 to 50 (plus several narrow petaloids) arranged regularly.

*Form.*—Cupped at first, becoming more flat in the center, with petals rolled loosely outward, and later at maturity rounded with higher center with petals rolled loosely outward and downward.

Petals: Fairly thick; satiny both inside and outside.

*Shape.*—Outside petals, broad lanceolate (almost round with pointed base); intermediate—lanceolate with acute tip; inside—lanceolate with acute tip.

Color: Newly opened flower from a plant grown outdoors (September 1968), Visalia, Calif.

*Outside petal.*—Outside surface—Mallow Purple 630/2 with yellow at base; inside surface—Roseine Purple 629/1 with yellow at base.

*Intermediate petal.*—Outside surface: Mallow Purple 630/2 with yellow at base; inside surface: Roseine Purple 629/1 (or slightly darker) with yellow at base.

*Inner petal.*—Outside surface—same as intermediate petal; inside surface—same as intermediate petal.

General color effect:

*Newly opened flowers.*—Soft lavender color, similar to but more lively than color of Sterling Silver (hybrid tea rose, Plant Pat. No. 1,433).

*Three days open.*—Soft lavender (lilac) color.

Behavior: As flowers age petals may become darker shade before dropping off. Spent petals drop off. Flower color often deeper in slight shade.

Flower longevity (September 1968): Bush in garden or pot 3 to 5 days. Cut flowers at living room temperature 3 to 4 days.

Reproductive organs:

*Stamens.*—Few to average, arranged irregularly about pistil; mixed with petaloids.

*Filaments.*—Short; yellow

*Pollen.*—Small amount; yellow.

*Pistils.*—Average number.

*Styles.*—Uneven; medium to short, bunched.

*Stigma.*—Nearly white.

*Ovaries.*—All enclosed in calyx.

*Hips.*—None.

*Sepals.*—Permanent; spear shaped; recurved (fold back against peduncle).

*Seeds.*—None.

Foliage:

*Leaves.*—Compound of five leaflets, sometimes seven; abundant; small to moderately small; leathery, semiglossy.

*Leaflets.*—Shape: lanceolate; apex acute; base acute or rounded acute. Margin serrate. Color: normal green; new growth sometimes lightly tinted bronze; serrated margins often tinted bronze. Rachis: medium strength; upper side smooth except for few very tiny prickles, grooved; under side sparsely thorny with few very tiny prickles. Stipules: fairly long; narrow; medium length narrow points which may turn out at both more or less than 45 degrees.

Growth:

*Habit.*—Dwarf; bushy; rounded; much branched.

*Growth.*—Free; vigorous.

*Canes.*—Medium; slender.

*Main stems.*—Color: dull green. Thorns: few; medium length; hooked slightly downward. Color: gray. Prickles: none. Hairs: none.

*Branches.*—Color: medium green. Thorns: sparsely thorny (or none); medium length; hooked slightly downward; medium length oval base. Prickles: none. Hairs: none.

*New shoots.*—Color: medium green, sometimes tinted bronze. Thorns: few to moderate (often none); medium length; hooked slightly downward, greenish to reddish color; sharp points; base oval. Prickles: none. Hairs: none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, rounded, much branched, bush type, as illustrated and described, characterized by buds and flowers resembling the Easter Morning (Plant Pat. 2,177) miniature rose in general form but usually with more open (less petals) flowers, the color being soft lavender rather than ivory white; the general color effect being lavender of a shade resembling Sterling Silver (hybrid tea, Plant Pat. No. 1,433); and further characterized by a plant which is of vigorous and compact growth, easy to propagate from cuttings, with small semi-glossy foliage, an abundance of bloom, with flowers borne singly or several to stem in loose clusters.

No references cited.

ROBERT E. BAGWILL, Primary Examiner